United States Patent [19]

Lundberg

[11] Patent Number: 5,686,660
[45] Date of Patent: Nov. 11, 1997

[54] CONSISTENCY TRANSMITTER

[75] Inventor: Peter Lundberg, Amal, Sweden

[73] Assignee: BTG Kalle Inventing AB, Sweden

[21] Appl. No.: 666,507

[22] PCT Filed: Nov. 22, 1995

[86] PCT No.: PCT/SE95/01395

§ 371 Date: Jun. 27, 1996

§ 102(e) Date: Jun. 27, 1996

[87] PCT Pub. No.: WO96/16322

PCT Pub. Date: May 30, 1996

[30] Foreign Application Priority Data

Nov. 23, 1994 [SE] Sweden .................. 9404064

[51] Int. Cl.$^6$ .................. G01N 11/16; G01N 11/00
[52] U.S. Cl. .................. 73/54.24; 73/53.03; 73/54.33
[58] Field of Search .................. 73/54.24, 54.33, 73/53.03, 54.23, 54.28, 54.25, 54.26

[56] References Cited

U.S. PATENT DOCUMENTS

| 2,701,469 | 2/1955 | Burns, Jr. | 73/59 |
| 3,364,730 | 1/1968 | Wall | 73/59 |
| 3,611,789 | 10/1971 | Lopas | 73/59 |
| 3,796,088 | 3/1974 | Gustafsson et al. | 73/59 |
| 4,062,226 | 12/1977 | Hietala | 73/63 |
| 4,148,215 | 4/1979 | Hofstetter, Jr. | 73/54 |
| 4,337,646 | 7/1982 | Fraleigh | 73/59 |
| 4,757,708 | 7/1988 | Hietaranta | 73/59 |
| 5,067,344 | 11/1991 | Fitzgerald et al. | 73/54 |
| 5,349,848 | 9/1994 | Driver | 73/54.28 |
| 5,369,987 | 12/1994 | Nettamo et al. | 73/54.23 |
| 5,503,003 | 4/1996 | Brookfield | 73/54.32 |
| 5,531,102 | 7/1996 | Brookfield et al. | 73/54.32 |

FOREIGN PATENT DOCUMENTS

| 2006119 | 10/1977 | Germany . |
| 0868474 | 9/1981 | U.S.S.R. . |

Primary Examiner—Michael Brock
Assistant Examiner—J. David Wiggins
Attorney, Agent, or Firm—Ostrolenk, Faber, Gerb & Soffen, LLP

[57] ABSTRACT

The invention relates to concentration measurement transmitters, more specifically to an arrangement for a static, blade-type transmitter, which includes a blade active in the medium to be measured and suspended by a spindle such that shear force moment at the blade is translated via the spindle to a measurement converter for determining fiber concentration in the medium, the converter preferably being situated in the transmitter housing, into which the spindle extends and is sealed against it with the aid of a lead-through. The latter includes a tube either integral with, or rigidly, cohesively fixed to it and extending downwards to the free end portion of the spindle carrying the blade, the spindle extending through the tube with a clearance enabling movement of the spindle necessary for the measurement converter for a turning movement of the spindle about a theoretical turning center substantially at the middle portion of the tube, to the free end portion of which tube the spindle is rigidly and sealingly fixed, whereby a seal in the lead-through is obtained across the clearance formed between the spindle and the tube, which does not affect the shear force moment translated to the converter and consequently not measurement accuracy either in terms of pressure sensitivity, temperature sensitivity and/or longitudinal forces prone to being transmitted along the spindle towards the measurement converter.

3 Claims, 2 Drawing Sheets

CONSISTENCY TRANSMITTER

BACKGROUND OF THE INVENTION

1. Field of the Invention

The present invention relates to concentration measurement transmitters, more specifically to an arrangement for a static blade-type transmitter, which includes a blade active in the medium to be measured and suspended by a spindle, such that shear force moment at the blade is translated, via the spindle, to a measurement converter for determining fiber concentration in the fiber slurry medium, this converter preferably being situated in the transmitter housing, into which the spindle also extends, and against which it is sealed with the aid of a lead-through included in the arrangement.

2. Description of the Related Art

There are today several different main groups of devices for measuring concentration in fiber suspensions. One of these groups covers the so-called static blade-type concentration measurement transmitters, hereinafter denoted "blade transmitters". It is generally considered that the transmitters of this group usually have a performance inferior to that of transmitters in the other groups. In the cellulose industry there are applications with different requirements, however, with respective to such as measurement accuracy, repeatability, sensitivity to flow, temperature and pressure. Blade transmitters have consequently become established on the market as a relatively large group. Since they are given comparatively unqualified measurement tasks, these transmitters have a low price level in relation to that for the other groups. In turn, this means that manufacturers are not able to justify technical solutions notably increasing the cost of existing devices. The result has been that the drawbacks always associated with blade transmitters still remain.

There are about ten different blade transmitter manufacturers supplying the world market at present. As mentioned above, it is generally recognized that these transmitters have lower performance than is to be found in transmitters from the other groups. In most cases users accept this situation, since the transmitters are selected for less demanding applications, and have a comparatively low price. However, breakdowns occurring too frequently and costing expensive production interruptions cannot be tolerated. In this respect users demand useful life spans comparable with those for transmitters in the higher price ranges. Large sensitivity to pressure and temperature are also factors only very reluctantly accepted by users.

The majority of defects in blade transmitters, leading to breakdowns and possible production losses, are those that can be traced to the arrangement permitting the spindle to enter the transmitter housing while isolating the dry housing interior from the wet medium being measured. This arrangement is generally denoted "lead-through" hereinafter. Some form of seal must be provided between these two environments, while the shear force moment, inter alia varying as the concentration of the fiber suspension acting on the blade, must be translated to a measurement converter in such a way that measurement accuracy is not degraded. On the accompanying drawings FIGS. 1 and 2 illustrate conventional methods of arranging the lead-through. The latter figure depicts a relatively recent implementation, but if the lead-through itself is examined it will be understood that no technical advance has been made for the last twenty years.

The known implementation in FIG. 1 illustrates the most usual lead-through. Without exception it is also provided with a bearing means, inter alia for taking up axial forces. The sealing element consists of a ring made from an elastomer suitable for the purpose. Correctly implemented, this element is not sensitive to pressure. On the other hand, it is often sensitive to temperature, since the elasticity of the elastomer varies with temperature, and the transmitters are implemented using the weighing balance principle. As will be understood, this means that the measuring principle cannot compensate for variations of the kind mentioned, nor for ageing of the elastomer in question. Due to the relatively aggressive environment fluorene rubber elastomers are often selected, which causes a special problem, i.e. hysteresis, which unfortunately is often inherent in high-quality elastomer types. Leads-through of this type require some form of damping, otherwise the noise level would be too great. In some cases this problem has been solved by a silicon-filled damping means disposed on the "dry" side of the lead-through. When such a system breaks down, which happens relatively often, it gives the user much trouble, although emergency operation of a transmitter with this kind of lead-through is relatively good, since possible leakage is relatively slow as a rule, thus affording a longer time for counteraction.

The known implementation of FIG. 2 is the latest addition to embodiments intended to solve the problems arising at the passage of the spindle into the housing. A strong diaphragm has been introduced for ensuring the sealing function. It has also been understood that sensing means cannot be placed on the diaphragm, as with other known structures, but in a way that eliminates the effect of rapid temperature variations as far as possible. A correct selection of a measurement converter should be satisfactory in this case. However, what has not been taken into consideration is the effect of pressure. In previously known implementations of the diaphragm type, the latter will vary its stiffness for a change in pressure, and either increase or decrease the movement achieved by the shear force moments, depending on whether pressure increases or decreases. It should be pointed out that diaphragm structures of the strong type discussed here are really most suitably used in combination with a wire strain gauge, and correctly applied, may constitute high-resolution measurement converters. Dependence on temperature gradient and pressure will be very difficult to master in any case. The implementation according to this method of solving the problems involved is therefore a compromise at the expense of the sensitivity to shear force variations of the transmitter. The measurement converter in the case in question is of the inductive type, and requires much larger movement to give a maximum output signal than what is required by a wire strain gauge.

SUMMARY OF THE INVENTION

The object of the present invention is to provide an arrangement for a transmitter of the kind mentioned in the introduction, where the drawbacks inherent in the known transmitters have been completely eliminated. Contrary to at least one of the implementations just described, the inventive implementation does not have any movable parts, thus minimizing breakdowns caused by wear. A thin, very flexible diaphragm type has been avoided for reasons connected with resistance to pressure. All diaphragm structures cause large problems due to their sensitivity to pressure. When the structure is made more robust for reducing the effect of pressure, this is done at the expense of sensitivity and measurement accuracy. The features distinguishing the invention are disclosed in the accompanying claims.

Due to the invention, there has now been achieved an arrangement in transmitters, which meets its purpose in an excellent manner, while at the same time has low manufacturing costs, well in agreement with those for the implementations already discussed. In accordance with the invention, the diaphragm has been substituted by a tube, dimensioned such that requisite movement is translated to the measurement converter, even for the least amount of shear force moment. Since the tube can take up large axial forces with negligible change in shape, sensitivity to pressure will also be negligible. Transmitters of this type are often dimensioned for a maximum pressure of 10 bar for the medium to be measured, but should temporarily withstand about 25 bar. From a first impression, there is the temptation to assume that a tube of the slender configuration required to obtain at its free end a movement sufficient to provide movement necessary for the transmitter would collapse at relatively low pressure. However, physical property calculations show that the tube will easily withstand 100 bar. Since the spindle is rigidly fixed at the "wet" end of the tube, e.g. by welding, there is achieved that the spindle acts for mechanical reinforcement of the movement, a contribution to which is made by the theoretical turning center of the movement being at the center of the slender part of the tube.

BRIEF DESCRIPTION OF THE DRAWINGS

The invention will now be described in more detail, and with reference to the accompanying drawings where.

DETAILED DESCRIPTION OF THE PREFERRED EMBODIMENTS

Figure 1:
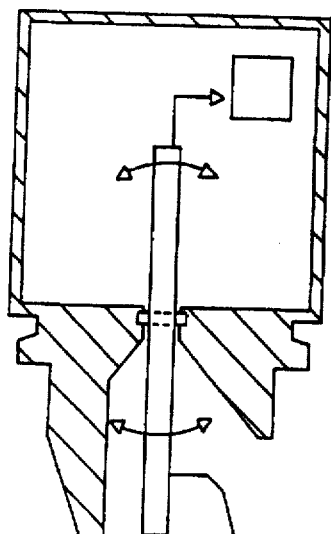
FIG. 1 schematically illustrates in a cross-sectional view a known blade transmitter according to a configuration having the most usual lead-through for the spindle, FIG. 2 similarly illustrates another known configuration, which is the latest addition to measures for solving spindle lead-through problems.
Figure 1:
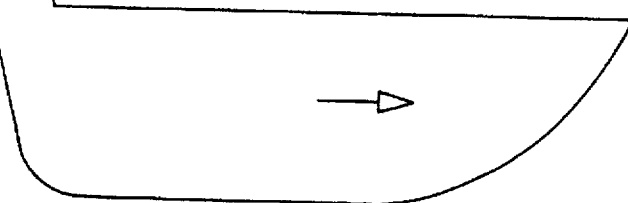
Figure 2:
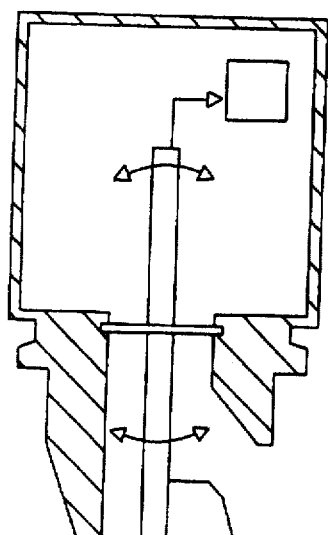
Figure 2:
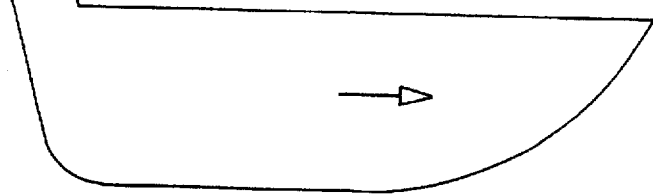
Figure 3:
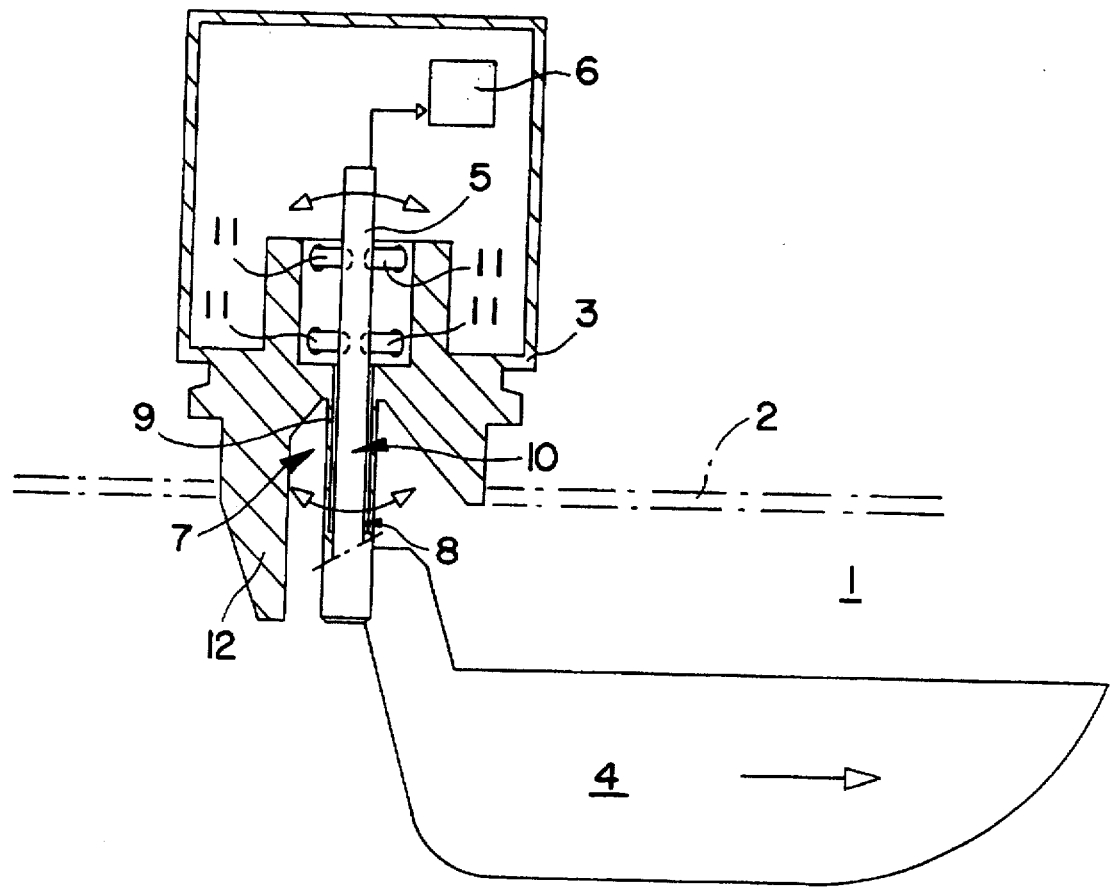
FIG. 3 is a schematic cross-section of a blade transmitter illustrating a preferred arrangement of the lead-through according to the present invention.

As will be seen in detail from FIG. 3, the arrangement in accordance with the invention includes a spindle 5, at its lower end connected to a blade 4 working in a medium 1 flowing in a pipe 2, on which the housing 3 is mounted in a suitable opening. Via the spindle 5, the blade 4 is intended to translate shear force moments, caused by the medium 1 flowing past the blade 4, to a measurement converter 6, disposed in the housing 6 and intended for determining fiber concentration in the medium in question.

The spindle 5 extends into the housing 3, and is sealed against it by a lead-through 7 included in the inventive arrangement. The lead-through 7 includes a thin-walled tube 9 downwardly extending from the housing 3 towards the bottom end portion of spindle 5 carrying the blade 4. In the illustrated embodiment the tube 9 is formed integral with the housing 3, which is fabricated from metal in this case. The spindle may alternatively be welded to, or otherwise rigidly fixed to the housing 3, with the prerequisite that there is no break in cohesion between the parts.

The spindle 5 extends through the tube 9 with clearance 8 enabling the translation of movement from the blade 4 to the converter 6. The tube 9 is also dimensioned so that even small shear force values are registrable at the converter 6. A theoretical turning center 10 occurs at the middle of the tube 9 on translation of a shear force moment via the spindle 5. The latter is rigidly fixed and sealed at the bottom portion of the tube 9, the lead-through 7 thus being provided with a seal that does not affect the moment translated to the converter 6, also signifying that measurement accuracy is not affected either.

Possible temperature gradients occurring as the result of rapid temperature variations with consequential variations in longitudinal expansion in the different parts of the structure do not affect the converter 6, assuming that a type suitable for the purpose has been selected. Only axial differences occur, and a correctly disposed converter, e.g. of differential capacitor or differential transformer type, will be insensitive to them.

Common to transmitters in the group discussed here is a tendency to be relatively sensitive to mechanical loading, which occurs when objects entrained in the medium flow impinge on the blade, these objects not being desired in the process. For at least partially protecting parts of the structure from damage a barrier means 12 is provided, this being a customary measure. In accordance with the invention the arrangement also includes at least one pair of diametrically opposed excess load protectors 11, but in a preferred embodiment four pairs are used, and they can be placed at 45° to the medium flow so that the greatest number of them participate in the intended protection against exceptional forces, irrespective of the direction taken by these undesired forces.

In summary, the invention provides a high-resolution transmitter that is not sensitive to temperature and pressure, while the risk for leakage in it has been eliminated. Furthermore, since the arrangement is not sealed against the medium by using movable seals with elastomers or the like, any deleterious effect over extended time periods due to ageing materials is averted.

What is claimed is:

1. An apparatus in static concentration measurement transmitters of a high-resolution type for analyzing fiber concentration in a fiber slurry medium, more specifically an apparatus for a static, blade-type transmitter in a housing designed for mounting onto a pipe wall, comprising:

a blade active in the fiber slurry medium to be measured;

a spindle on which said blade is suspended such that shear force moment generated at said blade is translated via said spindle;

a measurement converter for determining fiber concentration in said medium, said shear force moment being translated via said spindle to said measurement converter, said converter being situated in the housing of said transmitter, into which housing said spindle extends; and a lead-through included in said apparatus and sealing said spindle against said housing, wherein said lead-through includes a tube having a middle portion, a fixed end attached to said housing, and a free end disposed adjacent an attachment joint of said spindle with said blade, said tube being disposed either integral with said housing, or rigidly, cohesively fixed thereto and extending parallel to, concentric with, and towards the free end portion of the spindle carrying the blade, the spindle extending through the tube with a clearance enabling movement of the spindle necessary for said measurement converter during a fibrous fluid medium induced turning or bending movement of the spindle about a theoretical turning center substantially at the middle portion of the tube, to the free end portion of which tube the spindle is rigidly and sealingly fixed, whereby a seal in the lead-through is obtained across the clearance formed between said spindle and said tube, which does not affect the shear force moment translated to the measurement converter, and consequently also does not affect measurement accuracy, either in terms of pressure sensitivity, temperature sensitivity, and/or any longitudinal forces prone to being transmitted along said spindle towards said measurement converter.

2. An apparatus as claimed in claim 1, wherein at least one pair of diametrically opposed excess load protectors attached to at least one pair of receiving holes in the housing on either side of the spindle is placed a distance from the theoretical turning center such as to take up large, mechanical loads that may be transferred from the blade to the spindle due to said excessive force moment exerted on said blade upon immersion exposure within said medium.

3. An apparatus for measuring the static concentration of a fiber medium by means of a blade-type transmitter with a blade active in the medium to be measured; where the shear moment force generated at the blade suspended by a spindle is translated to a measurement converter situated in the housing of same transmitter, the apparatus comprising:

a spindle extending into the housing; and a lead-through serving to seal the spindle against the housing, the lead-through comprising a tube either integral with the housing or rigidly cohesively fixed thereto and extending towards the free end portion of the spindle;

wherein the spindle extends through the tube with a clearance sufficient to enable movement of the spindle necessary for the measurement converter during a turning or bending movement of the spindle about a theoretical turning center at the middle portion of the tube; and the spindle is rigidly and sealingly fixed to the free end portion of said tube, whereby a seal is obtained in the lead-through which does not affect the shear force moment translated to the measurement converter and also consequently does not affect the measurement accuracy of such apparatus.

* * * * *